United States Patent [19]

Brandely et al.

[11] Patent Number: 5,268,169

[45] Date of Patent: Dec. 7, 1993

[54] TREATMENT METHOD OF OVARIAN CANCER USING INTERFERON GAMMA

[75] Inventors: Maud Brandely; Danielle Lando, both of Paris, France

[73] Assignee: Roussel Uclaf, France

[21] Appl. No.: 867,778

[22] Filed: Apr. 13, 1992

Related U.S. Application Data

[63] Continuation of Ser. No. 472,730, Jan. 31, 1990, abandoned.

[30] Foreign Application Priority Data

Feb. 2, 1989 [FR] France ................. 88-01346

[51] Int. Cl.$^5$ ............................................. A61K 37/66
[52] U.S. Cl. ................................... 424/85.5; 530/828
[58] Field of Search .................... 424/85.5; 530/828

[56] References Cited

U.S. PATENT DOCUMENTS 4,650,674  3/1987  Aggarwai et al. .................. 424/85.5

FOREIGN PATENT DOCUMENTS 8705518  9/1987  World Int. Prop. O. .

OTHER PUBLICATIONS

Seminars in Oncology, vol. 18, No. 3, Jun., 1991, pp. 248–254 Markman.
Proc–Am Soc Clin Oncol 9:156 (1990), Abstracts, Pujade et al.
Am J Clin Oncol, vol. 11, 1988, pp. 465–469, Welander et al.
D'Acquisto et al, Journal of Clinical Oncology vol. 6 No. 4 Apr. 1988, 689–695.
Saito et al, Cancer Chemother Pharmacol (1987), 19:233–239.

*Primary Examiner*—Howard E. Schain
*Attorney, Agent, or Firm*—Bierman and Muserlian

[57] ABSTRACT

A method of treating ovarian cancer in warm-blooded animals comprising intraperitoneally administering to warm-blooded animals by perfusion a recombinant polypeptide of human gamma interferon type with a specific activity at least equal to $1 \times 10^7$ U/mg in an anticancer effective amount.

10 Claims, No Drawings

TREATMENT METHOD OF OVARIAN CANCER USING INTERFERON GAMMA

This is a continuation of Ser. No. 472,730 filed Jan. 31, 1990, now abandoned.

STATE OF THE ART

Gamma interferon, in addition to its anti-viral and anti-pyroliferative properties, possesses a powerful immunomodulatory activity which distinguishes it from $\alpha$ and $\beta$ interferons. It stimulates the phagocytic cells, enabling in particular the lysis of certain tumor cells. The study of the tolerance of gamma interferon in patients at the terminal stage of cancer has not led to observations of remissions from these cancers (Vadhan-Raj et al., (1986) J. Clin. Oncol., Vol. 4 (2), p. 137-146 and Van Dr Burg et al., (1985) J. Biol. Resp. Mod., Vol. 4, p. 264-272.

The effectiveness of gamma interferon on various fresh, human cancer cells, according to the so-called "human tumor cloning system" test described by Hamburger et al., was shown in Patent Application No. WO 87/05518, notably on ovarian cancer colonies. Following these observations, clinical studies were carried out, particularly with patients having cancer of the ovary. However, the effectiveness of the gamma interferon in vivo was not observed either for administration by intravenous route (Welander et al., Am. J. Clin. Oncol. (1988), Vol. 11 (4) p. 465-469), or according to a protocol using administration by intra-peritoneal route [D'Acquisto et al., J. Clin. Oncol. (1988), Vol. 6, p. 689-695]. Generally, it is recognized that the anti-cancerous action of gamma interferon necessitates its use in combination with other therapeutic agents [Saito et al., Cancer Chemother. Pharmacol. (1989), Vol. 19, p. 233-2391].

OBJECTS OF THE INVENTION

It is an object of the invention to provide a novel method of treating ovarian cancer in warm-blooded animals, particularly humans.

This and other objects and advantages of the invention will become obvious from the following detailed description.

THE INVENTION

The novel method of the invention of treating ovarian cancer in warm-blooded animals comprises intraperitoneally administering to warm-blooded animals by perfusion a recombinant polypeptide of human gamma interferon type with a specific activity at least equal to $1 \times 10^7$ U/mg in an anti-cancer effective amount.

These results are contrary to the absence of effectiveness report by D'Acquisto for a recombinant gamma interferon administered through perfusion by intra-peritoneal route in the treatment of refractory ovarian cancers. The invention describes the use of human gamma interferon in a treatment, the effectiveness of which is shown by a response rate of 58%, for an administration intra-peritoneally through perfusion, in patients with ovarian cancer having residual tumor lesions after exeresis surgery and chemotherapy.

The specific activity of the recombinant products used in the invention is at least equal to $1 \times 10^7$ U/mg, determined by the standard test by measurement of the anti-viral activity relative to an NIH scale on Wish human cells infected by the vesicular stomatitis virus, and enables the administration of effective doses which are lower than the tolerated maximum dose expressed in mg of product. The method of the invention therefore makes use of recombinant polypeptides having an activity of gamma interferon type and possessing a high degree of purity.

The pharmaceutical compositions prepared by the invention preferably contain a recombinant human gamma interferon, that is, obtained by the technology of recombinant DNA, for example as described by Gray et al., in Nature, (1982) Vol. 295, p. 503-508 or in Patent Application EP 77,670, alleles or derivatives of these products as described for example in Patent Application EP 161,504. Known purification techniques are then used, which enable the preparation of high-purity products. The gamma interferon is notably that obtained starting with a strain of E. coli and containing 143 amino acids corresponding to the sequence of natural gamma interferon with a supplementary N-terminal methionine.

Preferably, the polypeptide employed in the method, preferably gamma interferon, is administered at a dose of 10 to $50 \times 10^6$ U/M$^2$ per injection and more particularly the polypeptide employed, preferably gamma interferon, is administered at a dose of $20 \times 10^6$ U/M$^2$ per injection.

The polypeptide employed, preferably gamma interferon, is preferably administered repeatedly for at least two non-consecutive days per week and especially, is administered repeatedly for at least two months, for example for three months. The dose administered, the frequency of the injection and the duration of the treatment vary as a function of the condition of the patient but is usually $0.3 \times 10^6$ to $1.5 \times 10^6$ U/kg.

The polypeptide employed, preferably gamma interferon, is contained in a pharmaceutical composition, preferably lyophilized in dropping bottles with 0.2 to 1 mg of active principle and is re-constituted with distilled water for injection. The solution obtained is immediately diluted with a solute which contributes to the stability of the active principle during perfusion, for example sodium chloride at 0.9%.

In the following examples there are described several preferred embodiments to illustrate the invention. However, it should be understood that the invention is not intended to be limited to the specific embodiments.

EXAMPLE 1

An intra-peritoneal perfusion composition was prepared containing 1 mg of gamma interferon, 50 mg of excipient, 4.1 ml of sterilized water and 250 ml of aqueous 0.9% sodium chloride solution. The gamma interferon had a specific activity of $2 \times 10^7$ U/mg and was used at a dose of $20 \times 10^6$ U/M$^2$ twice a week for four months for a total of $720 \times 10^6$ U/M$^2$ and 36 mg/M$^2$ of gamma interferon.

EXAMPLE 2

In a study of patients having residual tumor lesions, the size of which varied from microscopic to more than 20 mm after treatment by chemotherapy and exeresis surgery, the effectiveness was evaluated at 20% complete response after a histological examination carried out during a second operation. The gamma interferon compositions of the invention were administered at doses of $20 \times 10^6$ U/M$^2$ or 1 mg/M$^2$ per injection at a rate of 2 injections per week for 2 to 4 months, intra-peritoneally according to an ambulatory method. The compositions used contained 1 mg of active principle which was perfused in the patient for a time not exceeding 2 hours after previous perfusion of dialysis fluid varying depending on the condition of the patient, from 1 to 2 liters and constituted by Dianeal® 137 with 1.36% of glucose from TRAVENOL.

The evaluation of the patients' responses was effected during a laparotomy by macroscopic and histological examination with biopsies of the previously affected sites and biopsies at random. For 12 re-evaluated patients, the following responses were obtained:

| Patient | Size of lesions | Duration of treatment (months) | Response (*) |
|---|---|---|---|
| 201 | $\geq 20$ | 4 months | S |
| 301 | micro | 3 months | P |
| 503 | micro | 4 months | CR |
| 801 | <5 | 4 months | P |
| 803 | <20 | 3 months | PR |
| 1001 | >20 | 4 months | S |
| 1002 | <20 | 3 months | CR |
| 1004 | <5 | 2.5 months | CR |
| 1101 | micro | 4 months | CR |
| 1102 | micro | 4 months | P |
| 1901 | micro | 4 months | PR |
| 1902 | micro | 4 months | PR |

(*)
S = stabilization
P = progression
CR = complete response
PR = partial response The results show 4 complete responses and 3 partial responses which is a response rate of 58%.

Various modifications of the method of the invention may be made without departing from the spirit or scope thereof and it is to be understood that the invention is intended to be limited only as defined in the appended claims.

What is claimed is:

1. A method of treating ovarian cancer in female humans comprising intraperitoneally administering to female humans in need thereof by perfusion a recombinant polypeptide of human gamma interferon type with a specific activity at least equal to $1 \times 10^7$ U/mg in an anti-cancer effective amount as the sole therapeutic agent.

2. The method of claim 1 wherein the polypeptide is gamma interferon.

3. The method of claim 1 wherein the polypeptide is administered at a dose of 10 to $50 \times 10^6$ U/M² per injection.

4. The method of claim 1 wherein the polypeptide is administered at a dose of $20 \times 10^6$ U/M² per injection.

5. The method of claim 1 wherein the polypeptide is administered on at least two non-consecutive days per week.

6. The method of claim 5 wherein the polypeptide is administered for a period of at least 2 months.

7. The method of claim 2 wherein the polypeptide is administered at a dose of 10 to $50 \times 10^6$ U/M² per injection.

8. The method of claim 2 wherein the polypeptide is administered at a dose of $20 \times 10^6$ U/M² per injection.

9. The method of claim 2 wherein the polypeptide is administered twice a week on non-consecutive days.

10. The method of claim 9 wherein the polypeptide is administered for a period of at least 2 months.

* * * * *